United States Patent [19]

Dhingra et al.

[11] Patent Number: 4,735,649

[45] Date of Patent: Apr. 5, 1988

[54] GAMETOCIDES

[75] Inventors: Om P. Dhingra, Creve Coeur; John E. Franz, Crestwood, both of Mo.; Geoffrey Keyes, King Ferry, N.Y.; Dale F. Loussaert, Ellisville; Cynthia S. Mamer, St. Peters, both of Mo.

[73] Assignee: Monsanto Company, St. Louis, Mo.

[21] Appl. No.: 780,050

[22] Filed: Sep. 25, 1985

[51] Int. Cl.$^4$ ............... A01N 57/12; A01N 57/14
[52] U.S. Cl. ................................ 71/86; 558/169
[58] Field of Search ............................. 71/86

[56] References Cited

U.S. PATENT DOCUMENTS 3,993,467 11/1976 Franz .................................. 71/86

Primary Examiner—Catherine L. Mills
Attorney, Agent, or Firm—David Bennett; Robert B. Martin

[57] ABSTRACT

Novel hydroxyalkylesters of N-phosphonomethylglycine have been identified which prove to be effective gametocides.

4 Claims, No Drawings

GAMETOCIDES

BACKGROUND OF THE INVENTION

This invention concerns compounds that have been found to be active as gametocides. These compounds are derivatives of N-phosphonomethylglycine, which is usually called glyphosate.

An effective gametocide is a compound that, when applied to a plant during sexual maturity, is capable of killing or effectively terminating the development of a plant's male gametes while leaving the plant's female gametes, or at least a significant proportion of them, capable of undergoing cross fertilization with subsequent high yields of fertile, viable hybrid seed.

Many compounds are capable of killing the male gametes of a plant, indeed almost any systemic herbicide is effective in this role. However most also kill the female gametes and the rest of the plant and are therefore ineffective gametocides. Additionally, while some compounds can be applied at rates such that substantially only the gametes are affected, most are found to be fairly non-discriminating regarding the sex of the gametes destroyed.

A requirement of the ideal gametocide, therefore, is that the application level at which male gametes are effectively destroyed should be significantly lower than that required to destroy also the female gametes. Thus a gametocide should be capable of being spray applied in the field without extraordinary precautions against accidental overdoses.

Other desirable characteristics may be dictated by the plant to be treated. As an example, wheat is by nature self-pollinating as the male and female gametes are found inside the same flower which remains closed until the male gametes release their pollen onto the female gametes to fertilize them. Thus, when the flower opens fertilization is normally essentially complete. For a gametocide to be useful on wheat it must, besides killing the male gametes, not interfere with the opening of the flower when the female gametes are ready to be fertilized such that fertilization by pollen from other wheat plants, perhaps of a different strain, can occur.

The utility of gametocides lies in precisely this area of plant hybridization. By causing pollination of one variety of a plant species by a different variety of the same species, a hybrid plant is obtained. By careful selection of the parents, hybrids can be obtained with specific combinations of desirable traits such as plant size, grain yield disease resistance, herbicide tolerance, climatic adaptation, plant growth regulator response, and so on.

Hybridization utilizing cytoplasmic male sterility is available and is often used to produce commercial hybrid corn seed. However, techniques using the cytoplasmic male sterility system can take years to develop lines to the point that commercial quantities of hybrid seed can be produced. Use of an effective gametocide significantly reduces this development time by fifty percent or more.

Some plants, such as corn, can be relatively easily hybridized without resort to genetic techniques because the organ containing the male gametes are exposed and can easily be removed. These systems leave the female gametes, when ready for fertilization, accessible to any foreign corn pollen that is deposited thereon. As indicated above, however, this is not the case with plants such as wheat in which the male and female gametes develop together inside the same closed flower.

The significance of an effective gametocide is therefore that it provides a tool for the development of advantageous hybrids of plants that hitherto have been very difficult to cross-pollinate.

The present invention provides a group of novel compounds that are found to possess the gametocidal utility described above. The best of these gametocides are very effective in the production of high yields of fertile hybrid seed.

DISCUSSION OF THE ART

Many derivatives of N-phosphonomethylglycine have been described in the patent and scientific literature. These compounds have been described in terms of their herbicidal, plant growth regulating or sucrose deposition enhancing characteristics.

Typical examples of this type of art include U.S. Pat. Nos. 3,799,758, 3,853,530, 4,140,513, 3,970,695, 4,047,926 and 4,035,176.

None of these patents however teach any gametocidal activity or the specific compounds that provide one aspect of the present invention.

Other patents have been published showing compounds claimed to have gametocidal activity. These include U.S. Pat. No. 4,345,934 (1-aryl-1,4-dihydro-4-oxo(thio)pyridazines) and European Patent Application No. 0029265 (azetidine derivatives). None however have been found or described that are glyphosate derivatives.

DESCRIPTION OF THE INVENTION

The compounds of the present invention have the formula

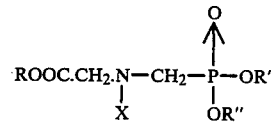

wherein R is hydrogen; a $C_1$–$C_4$ alkyl, hydroxyalkyl or chloroalkyl; or a $C_2$–$C_6$ alkoxyalkyl group; R' is a hydroxyalkyl group having from 2 to 8 carbon atoms and from 1–6 hydroxyl groups; R" is hydrogen or R'; and X is hydrogen or —COCF$_3$; as well as agronomically acceptable salts of such compounds.

The R' substituent is a hydroxyalkyl group and can contain from 1–6 hydroxyl groups. Generally it is found that better results are obtained when two or more hydroxyl groups are present. Thus preferred derivatives include glyceryl esters which may be esterified via the 1-, 2-, or the 3- hydroxyl group.

The preferred group R is also hydrogen but compounds having other R groups can be used. Such groups include alkyl, hydroxyalkyl and haloalkyl having from 1 to 4 carbon atoms and one or two halogen or hydroxyl groups. The preferred halogen is chlorine though bromine, fluorine or iodine could also be used. Alkoxy alkyls having a total of 2 to 6 carbon atoms, such as ethoxyethyl, can also be used.

In addition to the above compounds it is possible to use their agronomically acceptable salts. As will be noted the compounds of the invention are potentially amphoteric. Thus an acid such as hydrochloric acid can protonate the basic nitrogen atom or, if R or R" is hydrogen, a salt can be formed at one of these acidic hydrogens by reaction with a suitable base. In point of fact the use of a salt, particularly one in which the salt is formed by reaction with a base, is preferred since such salts are generally much more water-soluble than the corresponding acid. This makes application of the compounds significantly easier in practice.

Agronomically acceptable salts are salts in which the salt-forming moiety that reacts with the glyphosate derivative does not have any ecologically unacceptable consequences for the plant, the soil or the general environment. Acid that may form acceptable salts include hydrochloric acid, phosphoric acid and trifluoro acetic acid and bases include the alkali metal hydroxides and those based on the "onium" ions such as ammonium, organoammonium, sulfonium, sulfoxonium, phosphonium and oxonium.

The invention also comprises a process for the production of hybrid plants including monocotylodons such as rice, wheat, oats, barley and the like as well as dicotylodons such as soybeans. This process comprises applying a compound of the invention to a first plant species in an amount that is effective to sterilize essentially all the male gametes of the plant while leaving a significant proportion of the female gametes capable of fertilization; causing the female gamates to be fertilized by pollen from a second plant; and thereafter harvesting the hybridized seeds.

A secondary consequence of sterility in wheat is that the heads open so as to expose the female gametes. As a result they are fully accessible to pollen introduced from outside. Of course, if hybridization is planned, it is relatively easy to arrange that the pollen comes from a different wheat line.

The gametocide should preferably be applied after initiation of sexual development, but prior to sexual maturity, that is before pollen is shed from the anthers. Generally application in wheat should occur when the spike or head length is from 1 to 9 cm. and preferably 4 to 7 cm. in length. In other plants application should preferably be when the plants have reached a corresponding degree of sexual maturity.

The gametocides of the present invention when applied under optimum conditions kill essentially all, that is at least 95%, of all male gametes, while leaving a significant portion, by which is meant at least 40%, and often 60% or more of the female gametes capable of fertilization and the rest of the plant affected as little as possible.

The most preferred products achieve the desired effect over a wide range of application levels. This is referred to as showing a wide "application window". This is of course highly desirable when working in the field as accidental overdoses can easily occur. As will be noted the best compounds of the invention leave as much as 70% of the female gametes viable and have only a slight stunting effect on the plant as a whole.

The stunting effect is the result of the compounds having some phytotoxic activity that, at the levels of application used in connection with the present invention, is manifested by a reduction in the size of the plant and perhaps by a minor amount of chlorosis. Clearly the preferred gametocides of the invention are those in which these phytotoxic side effects are minimized.

EVALUATION OF GAMETOCIDES

The critical test for a gametocide is of course to apply it to a crop before fertilization occurs so as to kill the male gametes, allow cross fertilization with pollen from a second line, harvest the resulting seed, and grow this seed. This tests the extent to which the cross pollination has resulted in a viable hybrid. This, of course, takes a long time and makes the identification of an effective group of gametocides a difficult task. To cope with this problem a series of screens have been developed. The first screen, which can occur in a growth chamber or in a greenhouse during appropriate seasons, involves applying the gametocide and observing the effect on the plant. Those that eventually show good gametocidal activity are found to cause the flower to open wide (something that normally occurs only after the pollen from the male gametes is ready for discharge and fertilization has already occurred. This is known as showing "open head morphology". Parallel with this the best gametocides show only slight stunting of the plant.

Gametocides that survive this first screen are then subjected to the second screen in which they are applied to plants growing in a field. The rows are planted such that the treated rows can be fertilized by pollen from untreated rows of a different line. The seed from the cross-pollinated plants is harvested, planted and grown to assess the viability and degree of hybridization of the seed.

In a final evaluation, treated plants are followed to determine the degree of out-crossing that has occurred and the fertility of the resulting seed.

As will be seen from the data presented below, it is found that gametocides that perform well on the first screen generally show overall gametocidal activity. The compounds of the invention can be prepared by standard techniques known in the art such as those described in U.S. Pat. Nos. 4,053,505 and 4,218,235 processes.

DESCRIPTION OF PREFERRED EMBODIMENTS

In a modification of the process of U.S. Pat. No. 4,053,505 to illustrate a specific production sequence the glyceryl ester of glyphosate is prepared by reacting the ethyl ester of N-(dichlorophosphinyl-methyl) N-trifluoroacetyl glycine with 2,3-dibenzyloxypropyl alcohol in the presence of a base (triethylamine). This reaction product is then hydrolyzed using caustic soda and then acidified to generate the unesterified carboxylic acid group. Finally the benzyl ether groups are removed to yield hydroxyl groups using hydrogen and a 10% palladium on charcoal reduction catalyst with the reactant dissolved in acetic acid solution. This reaction sequence actually produces the isomer mixture employed in Example 1.

EXAMPLE 1

This Example details the gametocidal activity of a compound according to the invention on spring wheat in a growth chamber.

The awned hard red spring wheat cultivar "Anza" was grown in a growth chamber set at 70% humidity, and 21° C. (16 hour day, 8 hour night) until termination of the experiment. Light intensity was 800 uE. Seven seeds per six inch pot were planted in a soilless medium of Metro-Mix200 supplemented with 93 g Osmocote (14-14-14) Controlled Release Fertilizer, 93 g Peters (14-7-7) Slow Release Fertilizer, 17 g Micromax Micronutrients per cubic foot of Metro-Mix200. Approximately 10–14 days after planting, pots were thinned to six plants per pot. Chemical treatments were foliar applied using an enclosed track sprayer chamber consisting of a compressed air reservoir equipped with a manual speed adjustment and field sprayer nozzle (4002E). This method simulates actual field spraying techniques. The test consisted of using three rates on three dates in an aqueous carrier solution containing 0.2% Tween20 (a commercial surfactant) sprayed at a rate equivalent to 2805 liters/hectare. Untreated controls were included for comparison. After spike emergence and before anthesis, glassine bags were placed over approximately 12–15 heads per pot to prohibit all but self-pollination. When seeds were large enough to be easily seen and stigmas senesced (approximately 4 weeks after heading), bagged and unbagged spikes were evaluated for the number of seed set and observations on phytotoxicity recorded.

The compound was a glycerol ester of N-phosphonomethyl glycine. Analysis showed the compound to be a mixture of two isomers as follows:

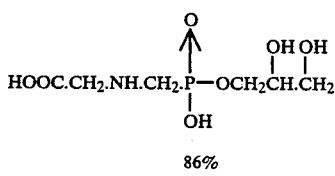

86% and

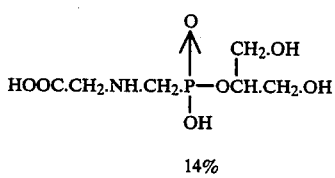

14%

The treatment dates, evaluation parameters and terminology explanations are as follows:
Rates: 5.6, 11.2, 16.8, Kg/H
Comments: Observations on evidence for biological activity determined at time of bagging.
Tot.Hds: Total number of heads per pot
PS:
  PS = % of heads >85% sterile (equal to P100+PP)
  P100 = % of heads 100% sterile (i.e. [# heads with 0 seeds/head]/[total # heads])
  PP = % of heads >85% but <100% sterile (i.e. typically [# heads with 1 to 5 seeds/head]/[total # heads])
Height: Mean culm length in centimeters of all tillers
Notes: Additional observations taken during scoring seed set

| Dates: | Spraydates (Spike Length) | | |
|---|---|---|---|
| Planted = 8-16 | D1 = 9-20 | (1.76 cm) | |
| Heading = 10-01 | D2 = 9-24 | (4.92 cm) | |
| Bagging = 10-01 thru 10-17 | D3 = 9-26 | (7.3 cm) | |

The mean % male sterility was determined to be as follows:

| | Spray Date | | |
|---|---|---|---|
| Rate | D1 | D2 | D3 |
| 5.6 | 79 | 100 | 100 |
| 11.2 | 87 | 100 | 100 |
| 16.8 | (No Heads) | 100 | 86 |

Control: Out of 80 bagged spikes from 6 pots, 4 spikes (5%) were sterile.

The detailed results on which this is based are shown on Table I.

TABLE I

| Rate: | Rep* | Comments | Tot. Hds. | Bagged No. | Bagged PS(P100 + PP) | Unbagged No. | Unbagged PS(P100 + PP) | Ht. (cm) | Notes |
|---|---|---|---|---|---|---|---|---|---|
| 5.6 Kg/H | | | | | | | | | |
| Date:D1 | 1 | MOD.STUNT,SK + AWN DIS.,SL.DEV. | 24 | 16 | 100(100 + 0) | 8 | 100(100 + 0) | 35 | SL.HEAD DISTORTION ONE HD. EPINASTY |
| | 2 | SL.YELLOWER L.Hds. | 23 | 12 | 58(33 + 25) | 11 | 45(0 + 45) | 45 | |
| Date:D2 | 1 | SL.STUNT,SL.DEV. | 17 | 6 | 100(50 + 50) | 11 | 99(90 + 9) | 35 | DIST., CUP SHAPED |
| | 2 | SL.DEV. | 21 | 13 | 99(84 + 15) | 8 | 87(87 + 0) | 43 | MOST NOT FULLY OUT OF BOOT |
| Date:D3 | 1 | SL.TO MOD.STUNT,SL.DEV. | 21 | 9 | 100(100 + 0) | 12 | 100(100 + 0) | 40 | |
| | 2 | SL.STUNT | 21 | 10 | 100(70 + 30) | 11 | 99(90 + 9) | 35 | SIX HEADS TOTALLY IN BOOT NOT SCORED |
| 11.2 Kg/H | | | | | | | | | |
| Date:D1 | 1 | SD,MOD.TO SEV. STUNT,YELLOWING OF LLVS + HDS, 10/8 = 10H | 21 | 16 | 74(62 + 12) | 5 | 60(60 + 0) | 37 | SPOTTY FERT. |
| | 2 | SEV.STUNT,NO HDS. | 13 | 6 | 100(100 + 0) | 7 | 100(100 + 0) | 20 | DEFORMED HDS. |
| Date:D2 | 1 | SL.STUNT,FEWER HDS/POT,SL.DEV. | 12 | 2 | 100(100 + 0) | 10 | 100(100 + 0) | 26 | ALL STILL IN BOOT, MANY CUP SHAPED |
| | 2 | SL.STUNT,NO HDS. | 12 | 2 | 100(100 + 0) | 10 | 100(100 + 0) | 24 | NONE OUT OF BOOT, CUP SHAPED |
| Date:D3 | 1 | SL.STUNT,NO HDS. EMERGED,SL.DEV. | 11 | 6 | 100(100 + 0) | 5 | 100(100 + 0) | 30 | NONE FULLY OUT OF BOOT, LVS HAVE |

TABLE I-continued

| Rate: | Rep* | Comments | Tot. Hds. | Bagged No. | Bagged PS(P100 + PP) | Unbagged No. | Unbagged PS(P100 + PP) | Ht. (cm) | Notes |
|---|---|---|---|---|---|---|---|---|---|
| | 2 | SL.STUNT,SL.DEV. 10/8 = 20H | 8 | 6 | 100(100 + 0) | 2 | 100(50 + 50) | 30 | PURPLE TINGE SIX PLANTS FULLY IN BOOT |
| 1.68 Kg/H Date:D1 | 1 | SEV.STUNT,NO HDS, YELLOW-GREEN COLOR | 1 | 1 | 0(0 + 0) | 0 | 0(0 + 0) | 15 | ONLY ONE HD. EMERGED-REST OF PLANT DEAD |
| | 2 | SEV.STUNT, YELLOWING,NO HDS | 0 | 0 | 0(0 + 0) | 0 | 0(0 + 0) | 25 | NO HEADS |
| Date:D2 | 1 | SL.TO MOD.STUNT, FEW HDS | 9 | 1 | 100(100 + 0) | 8 | 100(100 + 0) | 20 | NONE FULLY OUT OF BOOT |
| | 2 | MOD.STUNT,FEW HDS IN BOOT, NO HDS.OUT | 6 | 1 | 100(100 + 0) | 5 | 100(100 + 0) | 17 | CUP SHAPED, FEW HEADS |
| Date:D3 | 1 | SL.STUNT,SL.DEV | 14 | 9 | 77(77 + 0) | 5 | 80(80 + 0) | 35 | MANY HEADS SILL INSIDE BOOT |
| | 2 | SL.STUNT,SL.DEV | 21 | 9 | 100(100 + 0) | 12 | 100(100 + 0) | 33 | NONE FULLY OUT OF BOOT |

*Replication No.

From the above it can be seen that the compound showed excellent male sterility through if the application is made too early there is a reduction in normal spikes appearing from the boot.

EXAMPLE 2

The same compound as was evaluated in Example 1 was tested in the field on three different wheat varieties on five different dates (D1-D5) and at four different levels. The observations were reported in terms of height, vegetative damage (0=Plot completely damage; 100=No damage to plot), percent sterility, grain yield (in grams of seed per three foot row), and in percentage of seed obtained that was in fact hybridized.

The varieties and the spray dates were as follows:

| Variety | Spray Date | Spike Length Range | Calendar Date |
|---|---|---|---|
| DK 235 | D1 | 1-2 mm | May 9 |
| | D2 | 10-20 mm | May 17 |
| | D3 | 22-32 mm | May 19 |
| | D4 | 30-40 mm | May 21 |
| | D5 | 35-45 mm | May 23 |
| McNair 1003 | D1 | 4 mm | May 9 |
| | D2 | 12-20 mm | May 18 |
| | D3 | 25-28 mm | May 19 |
| | D4 | 30-43 mm | May 23 |
| | D5 | 38-62 mm | May 24 |
| Vona | D1 | 4 mm | May 9 |
| | D2 | 8-14 mm | May 16 |
| | D3 | 10-17 mm | May 18 |
| | D4 | 18-32 mm | May 21 |
| | D5 | 24-54 mm | May 23 |

Field grown winter wheat plants were used to examine potential gametocide activity. The procedures for evaluating the gametocide were as follows.

Experimental plots were four feet long and seven rows wide consisting of both male and female rows. The female rows or spray rows were the center three rows and consisted of cultivars that contained either the Rht1 or Rht2 dwarfing gene. These rows were bordered by two rows, which were male rows or the pollen source. The male rows contained a mixture of cultivars varying in date of anthesis that did not contain either of the dwarfing genes and were of "normal" height.

All of the cultivars were seeded with a Marliss grain drill at a rate of 112 Kg per hectare which is standard for the area and growing conditions. No herbicide was applied to the plots and minor weeding was done by hand. Fall application of fertilizer consisted of 28, 140, and 140 Kg per hectare of nitrogen, phosphorus, and potassium as ammonium nitrate, superphosphate, and muriate potash, respectively. In the early spring at greenup of the wheat an additional 56 Kg of nitrogen per hectare was applied as a 28% nitrogen solution (UAN) adjusted to pH6 with concentrated HCl. Di-syston 8 (1.17 liters/hectare was applied on 19 April for aphid and greenbug control. Malathion (1.12 Kg ai/hectare) and Bayleton 50% WP (0.2 Kg ai/hectare) was applied with an aerial application of 46.75 liters/hectare at the late boot stage of development to control insects and leaf rust, respectively.

The experimental design consisted of a split-split plot design with cultivars as main blocks and dates of application as sub-blocks. Compounds and rates were randomized within the splits. The field layout grouped the treatment combinations such that the treatments applied on the same date were adjacent. Timing of application was based on spike length and ranged from double ridge to spikes lengths equal to 5 cm which would make the stage of plant development in the early jointing to early boot stage. Spikes were excised from a sample of the most mature tillers at regular intervals and the spike lengths were used to monitor ear development.

Treatments were foliarly applied to the female rows using a spray boom mounted to a high-clearance tractor with a single spray nozzle directly above each of the spray rows. Treatment chemicals were formulated in water and included 0.2% Tween20 as a surfactant. Applications were made with a solvent volume equivalent to approximately 701.25 liters per hectare.

Data collection: Glassine bags were placed on 25-30 spikes per plot to determine the level of male sterility. The glassine bags (5-8 bags/day) were placed on the spikes after head emergence but prior to anthesis (anther extrusion). The bags were stapled and left in place to prevent all but self-pollination from occurring. About four weeks later after the seeds were in a soft-hard dough stage of development the bags were collected and scored for seed set. Three classifications of seed set were used in scoring the bags: 100% sterility—no seed set on the spike, partial sterility—<15% seed set or approximately 1-5 seeds per spike, or fertile spikes—>15% seed set. After anthesis, observations were made on vegetative damage, "open heads", spike distortion, and head emergence. Prior to harvest culm height was measured by determining an average culm height for each plot.

Grain yield was determined by hand harvesting the entire female plot and threshing with a Vogel thresher. A sub-sample of the grain was used in a GA test (40 mg/pot) to determine hybrid seed set. Plants were scored for responsiveness to GA approximately two weeks after seeding. Hybrid seed produced by crossing pollen from the male rows onto the sterile female stigmas will have elongated internodes after being grown in the GA solution. Only plots that had shown significant male sterility under bagged heads were tested for hybrid seed set.

The results obtained were as follows:

TABLE II

| Rate Kg/H | Height cm | Vegetative Damage | Sterility % | Grain Yield G/Meter | Hybrid Seed (%) |
|---|---|---|---|---|---|
| McNair 1003 (Control) | 66 | 100.0 | 1.8 | 98.4 | 0 |
| Spray Date: D2 | | | | | |
| 1.68 | 50 | 35.0 | 74.0 | 36.3 | 9 |
| Spray Date: D3 | | | | | |
| 1.68 EQ | 57 | 48.3 | 4.3 | 54.6 | 4 |
| 3.36 EQ | 53 | 43.3 | 50.0 | 38.4 | 35 |
| 5.04 EQ | 43 | 36.7 | 75.3 | 15.5 | 28 |
| 6.72 EQ | 34 | 12.5 | 88.0 | 2.1 | 34 |
| Spray Date: D4 | | | | | |
| 1.68 EQ | 66 | 95.0 | 9.3 | 87.0 | 5 |
| 3.36 EQ | 59 | 56.7 | 63.7 | 45.1 | 41 |
| 5.04 EQ | 46 | 36.7 | 84.0 | 19.8 | 52 |
| 6.72 EQ | 39 | 11.7 | 93.3 | 3.0 | 62 |
| Spray Date: D5 | | | | | |
| 1.68 EQ | 63 | 91.7 | 4.0 | 76.3 | 4 |
| 3.36 EQ | 57 | 73.3 | 46.0 | 62.3 | 36 |
| 5.04 EQ | 47 | 66.7 | 63.3 | 36.7 | 50 |
| 6.72 EQ | 42 | 46.7 | 76.3 | 19.5 | 44 |
| DK235-CMS | | | | | |
| Spray Date: D2 | 60 | 100.0 | 99.2 | 61.9 | 69 |
| Spray Date: D4 | 62 | 100.0 | 98.2 | 55.4 | 81 |
| VAR: DK235 (Control) | 62 | 100.0 | 4.1 | 115.2 | 0 |
| Spray Date: D2 | | | | | |
| 1.68 EQ | 49 | 61.7 | 60.0 | 62.8 | 3 |
| 3.36 EQ | 29 | 7.5 | 82.0 | 6.9 | 2 |
| 5.04 EQ | 30 | 3.5 | 90.5 | 1.7 | 7 |
| 6.72 EQ | 28 | 2.0 | 92.0 | .0 | — |
| Spray Date: D3 | | | | | |
| 1.68 EQ | 59 | 98.3 | 10.3 | 116.5 | 3 |
| 3.36 EQ | 53 | 71.7 | 55.0 | 61.1 | 11 |
| 5.04 EQ | 40 | 41.7 | 69.3 | 27.9 | 16 |
| 6.72 EQ | 36 | 17.3 | 79.0 | 15.6 | 11 |
| Spray Date: D4 | | | | | |
| 1.68 EQ | 63 | 100.0 | 5.3 | 115.1 | 0 |
| 3.36 EQ | 61 | 100.0 | 31.7 | 95.7 | 3 |
| 5.04 EQ | 59 | 100.0 | 32.7 | 83.5 | 10 |
| 6.72 EQ | 57 | 80.0 | 31.7 | 75.4 | 9 |
| Spray Date: D5 | | | | | |
| 1.68 EQ | 65 | 100.0 | 8.3 | 119.0 | 0 |
| 3.36 EQ | 58 | 96.7 | 48.7 | 69.8 | 11 |
| 5.04 EQ | 59 | 85.0 | 75.0 | 58.7 | 23 |
| 6.72 EQ | 51 | 70.0 | 86.3 | 29.9 | 42 |
| VONA-CMS | | | | | |
| Spray Date: D2 | 59 | 100.0 | 98.0 | 49.4 | 79 |
| Spray Date: D4 | 59 | 100.0 | 97.0 | 52.2 | 77 |
| VONA (Control) | 59 | 100.0 | 2.0 | 87.3 | — |
| Spray Date: D2 | | | | | |
| 1.68 EQ | 46 | 63.3 | 42.7 | 39.2 | 6 |
| 3.36 EQ | 27 | 3.0 | 90.0 | .4 | 15 |
| 5.04 EQ | 25 | .0 | 92.5 | .1 | 31 |
| Spray Date: D3 | | | | | |
| 1.68 EQ | 34 | 26.7 | 84.0 | 11.2 | 6 |

TABLE II-continued

| Rate Kg/H | Height cm | Vegetative Damage | Sterility % | Grain Yield G/Meter | Hybrid Seed (%) |
|---|---|---|---|---|---|
| Spray Date: D4 | | | | | |
| 1.68 EQ | 51 | 100.0 | 22.0 | 66.6 | 6 |
| 3.36 EQ | 36 | 15.0 | 88.0 | 7.0 | 27 |
| 5.04 EQ | 33 | 3.5 | 93.5 | 1.3 | 8 |
| Spray Date: D5 | | | | | |
| 1.68 EQ | 59 | 100.0 | .0 | 97.2 | 2 |
| 3.36 EQ | 54 | 100.0 | 13.0 | 78.6 | 3 |
| 5.04 EQ | 53 | 76.7 | 36.7 | 47.4 | 15 |
| 6.72 EQ | 43 | 50.0 | 54.0 | 26.0 | 14 |

EXAMPLE 3

This Example shows that the compound evaluated in Examples 1 and 2 has gametocidal activity also in rice.

Materials and Methods

The rice cultivar S-201 (Japanicum rice) was grown in a greenhouse set at ambient conditions with no additional lighting. Ten to twelve seeds per six inch holeless pot were planted in a soilless medium of Metro-Mix200 supplemented with Oscomote (14-14-14) Controlled Release Fertilizer, Peters (14-7-7) Slow Release Fertilizer and Micromax Micronutrients. Pots were then covered with a sheet of cellophane to reduce soil evaporation. The cellophane was removed 4-5 days after the seedlings had emerged. Pots were later thinned to six plants per pot. Eight weeks after planting 0.12 g of Sequestrene Fe was added to each pot after the appearance of Fe deficiency. Fourteen weeks after planting 1.5 g of Peters (20-19-18) Soluble Fertilizer was added to each pot. Chemical treatments were foliar applied using an atomizer and compressed air in a test using four rates on four dates in a 15 ml carrier solution of 100% H20-0.2% Tween20.* Untreated controls were included for comparisons. Approximately twenty-one weeks after planting, plants were evaluated for percentage seed set and observations on vegetative phytotoxicity recorded.
*Experimental Units 908,918,940 Carrier solution=10 mls.

Pot: Pot number
PS: Percent sterility where sterility is equal to the approximate percentage of kernels in the green panicles which were sterile.
Panicle Observations:
N = normal appearing panicle, W = white panicle where panicle is totally sterile and appears to have dried up.
Emergence of panicle from the boot:
fully emerged- panicle totally out of the boot
0 fully emerged- only partial emergence of panicle from boot
0 emerged- no panicles emerged from boot
Vegetative Damage:
VD = vegetative damage
LF TIP CHL = leaf tip chlorosis
SL = slight, SEV = severe, MOD = moderate, V SL = very slight
Treatment with the compound occurred as follows:
Rates: 2.8, 5.6, 8.4 and 11.2 Kg/H
Dates: Planted = July 2
Spraydates D1 = Sept. 10
D2 = Sept. 17
D3 = Sept. 19
D4 = Sept. 19
D5 = Sept. 20
Heading Date = Sept. 21

-continued

Results: Table III contains the detailed observations.

Summary:
The compound tested was an active male sterilant on rice. Early applications (D1-approximately 1-cm panicle length) at high rates (5.6–11.2 Kg/H) resulted in a reduction in plant height, severe vegetative damage, and a failure of the majority of the panicles to emerge from the boot. Even at the 2.8 Kg/H rate there was a significant reduction in the number of panicles per pot on the D1 spray date.

Later dates [D2-D4(late boot)] of application showed slight to moderate vegetative damage depending on the rate, but the vegetative damage was significantly less than the D1 applications.

TABLE III

| | Pot | PS | Panical Obs. | Vegetative Damage |
|---|---|---|---|---|
| Rate: 0.0 Kg/H | | | | |
| Date: 1 | 949 | 0% | 17N-ALL FULLY EMERG | NO VD, SOME LF TIP CHL |
| Date: 2 | 950 | 0% | 21N-ALL FULLY EMERG | NO VD, SOME LF TIP CHL |
| Date: 3 | 951 | 0% | 26N-ALL FULLY EMERG | NO VD, SOME LF TIP CHL, MANY NEW TILLERS |
| Date: 4 | 952 | 0% | 16N-ALL FULLY EMERG | NO DV, SOME LF TIP CHL |
| Rate: 2.8 Kg/H | | | | |
| Date: D1 | 940 | >90% | 4N-) FULLY EMERG | SL.VD, LF TIP CHL, MANY NEW TILLERS |
| | 918 | <50% | 3W, 8N-MOST HAVE EMERG | SL.VD, V.SL.LF TIP CHL, MANY NEW TILLERS |
| | 908 | 100% | 1W, 3N-0 FULLY EMERG | SL.VD, LF TIP NEC, MANY NEW TILLERS |
| Date: D2 | 943 | >50% | 1W, 17N-0 EMERG | NO VD, LF TIP CHL |
| | 902 | <50% | 1W, 12N-MANY NOT FULLY EMERG | NO VD, THIN STAND, LF TIP CHL |
| | 925 | >50% | 14N-0 FULLY EMERG | NO VD, LF TIP CHL |
| Date: D3 | 915 | >50% | 4W, 13N-MOST HAVE EMERG | VD = 0 TO V.SL. |
| | 933 | <75% | 2W, 19N-MOST HAVE EMERG | NO VD, LF TIP CHL |
| | 924 | <50% | 3W, 11N-SEVERAL EMERGED | NO VD, LF TIP CHL |
| Rate: 2.8 Kg/H | | | | |
| Date: D4 | 911 | >50% | 17N-0 FULLY EMERG | SL, VD, LF TIP CHL, A FEW NEW TILLERS |
| | 945 | <50% | 3W, 14N-2 HAVE EMERG | SL.VD, LF TIP CHL, MANY NEW TILLERS |
| | 932 | <75% | 2W, 15N-MANY FULLY EMERG | V.SL.VD, LF TIP CHL, MANY NEW TILLERS |
| Rate: 5.6 Kg/H | | | | |
| Date: D1 | 939 | 100% | 4N-0 EMERG | SL. VD, LF TIP CHL |
| | 907 | | NO PANICLES | MOD. VD, CHL |
| | 919 | | NO PANICLES | MOD. VD, CHL |
| Date: D2 | 926 | >50% | 2W, 13N-0 FULLY EMERG | NO VD, SL. CHL |
| | 941 | 100% | 1W, 16N-0 FULLY EMERG | V. SL. VD, SL. CHL |
| | 904 | >50% | 5W, 9N-0 FULLY EMERG | NO VD, LF TIP CHL |
| Date: D3 | 921 | >50% | 7W, 7N-0 FULLY EMERG | SL. VD, LF TIP CHL |
| | 913 | >50% | 10W, 5N-2 HAVE EMERG | SL. VD, LF TIP CHL |
| | 934 | 100% | 7W, 7N-0 FULLY EMERG | NO VD, LF TIP CHL |
| Date: D4 | 910 | >75% | 7W, 7N-0 FULLY EMERG | SL.VD, LF TIP CHL.F FEW NEW TILLERS |
| | 930 | >75% | 3W, 10N-0 FULLY EMERG | SL.VD, SL. CHL, A FEW NEW TILLERS |
| | 946 | <>50% | 11W, 9N-0 FULLY EMERG | V.SL.VD, LF TIP CHL, MANY NEW TILLERS |
| Rate: 8.4 Kg/H | | | | |
| Date: D1 | 937 | | NO PANICLES | SEV. VD, NECR |
| | 906 | | NO PANICLES | SEV. VD, NECR |
| | 917 | | NO PANICLES | SEV. VD, CHL, LF TIP NECR |
| Date: D2 | 903 | 100% | 4W, 8N-0 FULLY EMERG | V. SL. VD, LF TIP CHL |
| | 928 | >75% | 2W, 11N-1 EMERGED | V. SL. VD, SOME CHL |
| | 942 | 100% | 8W, 5N-0 EMERG | V. SL. VD, LF TIP CHL |
| Date: D3 | 935 | >90% | 9W, 5N-0 FULLY EMERG | SL. VD, LF TIP CHL |
| | 914 | 100% | 10W, 7N-0 FULLY EMERG | V. SL. VD, LF TIP CHL |
| | 922 | 100% | 5W, 13N-0 EMERG | MOD. VD, LF TIP NECR |
| Date: D4 | 948 | 100% | 8W, 6N-0 FULLY EMERG | SL. VD, SOME CHL, A FEW NEW TILLERS |
| | 931 | 100% | 7N-0 EMERG | SL. VD, CHL |
| | 909 | 100% | 2W, 1N-0 EMERG | SL. VD, CHL |
| Rate: 11.2 Kg/H | | | | |
| Date: D1 | 938 | | NO PANICLES | SEV. VD, NECR |
| | 920 | | NO PANICLES | SEV. VD, NECR. |
| | 905 | | NO PANICLES | SEV. VD, CHL, LF TIP NECR |
| Date: D2 | 944 | >50% | 7W, 9N-A FEW EMERG | V. SL. VD, LF TIP CHL |
| | 927 | 100% | 1W, 5N-0 EMERG SEV DISEASE | SL. VD, SOME CHL |
| | 901 | >90% | 2W, 8N-0 EMERG | NO VD, LF TIP CHL |
| Date: D3 | 923 | 100% | 14W, 2N-0 FULLY EMERG SEV DISEASE | SL. VD, LF TIP CHL |
| | 936 | >90% | 6W, 9N-0 FULLY EMERG | SL. VD, LF TIP CHL |
| | 916 | 100% | 10N-0 EMERG SEV DISEASE | V. SL. VD, SOME CHL |
| Rate: 11.2 Kg/H | | | | |
| Date: D4 | 912 | 100% | 7W, 10N-0 EMERG | SL. VD, CHL |
| | 947 | 100% | 5W, 6N-0 EMERG | SL. VD, SOME CHL |
| | 929 | 100% | 2W, 2N-0 EMERG | SL. VD, CHL |

EXAMPLE 4

This Example shows the application of the compound tested in Examples 1 to 3 is a gametocide for dicotyledonous plants such as soybeans.

A field experiment was conducted in which 1.12 and 5.6 Kg/H of the compound was applied to (cv Nathan, MGV) soybean at first flower appearance (on August 10). Pollen was sampled on August 29 and viability was measured using the I-KI starch test. The 1.12 Kg/H rate contained 75–95% viable pollen compared to a control. No viable pollen was detected in plants treated at the 5.6 Kg/H rate. Observations on November 2 indicated the plants treated at the higher rate were functionally sterile, i.e., they had few or no pods.

EXAMPLE 5

This Example details the evaluation of the herbicidal activity of (A) the bis(2-hydroxyethyl)ester of glyphosate and (B) the mono (2-hydroxyethyl)ester of glyphosate.

The procedure used was the same as that described in Example 2. The evaluation was conducted on the same varieties of wheat and spraying was performed on the same spray dates.

The results obtained are set forth on Table IV.

TABLE IV

| Rate Kg/H | Height cm | Vegetative Damage | Sterility % | Yield G/Meter | Hybrid Seed (%) |
|---|---|---|---|---|---|
| A DK235 Control | 62 | 100.0 | 4.1 | 115.2 | — |
| Spray Date: D2 | | | | | |
| 1.68 EQ | 53 | 93.3 | 15.3 | 79.5 | 2 |
| 3.36 EQ | 46 | 21.7 | 63.3 | 28.1 | 8 |
| 5.40 EQ | 31 | 3.5 | 84.5 | 2.2 | 2 |
| 6.72 EQ | 28 | 3.5 | 80.5 | 2.4 | 4 |
| Spray Date: D3 | | | | | |
| 1.68 EQ | 58 | 93.3 | 2.0 | 100.1 | 1 |
| 3.36 EQ | 51 | 55.0 | 44.0 | 62.8 | 11 |
| 5.40 EQ | 43 | 25.0 | 58.7 | 30.6 | 11 |
| 6.72 EQ | 35 | 11.7 | 70.0 | 9.6 | 21 |
| Spray Date: D4 | | | | | |
| 1.68 EQ | 65 | 100.0 | 6.7 | 106.4 | 0 |
| 3.36 EQ | 62 | 98.3 | 9.3 | 89.4 | 2 |
| 5.40 EQ | 60 | 93.3 | 20.7 | 95.5 | 0 |
| 6.72 EQ | 55 | 70.0 | 22.3 | 70.9 | 8 |
| Spray Date: D5 | | | | | |
| 1.68 EQ | 64 | 100.0 | 2.0 | 117.2 | 1 |
| 3.36 EQ | 63 | 100.0 | 8.0 | 104.9 | 1 |
| 5.40 EQ | 58 | 71.7 | 29.3 | 73.8 | 4 |
| 6.72 EQ | 58 | 48.3 | 31.7 | 62.6 | 8 |
| B DK235 Control | 62 | 100.0 | 4.1 | 115.2 | — |
| Spray Date: D2 | | | | | |
| 1.68 EQ | 55 | 100.0 | 19.3 | 89.4 | 2 |
| 3.36 EQ | 45 | 35.0 | 56.0 | 43.5 | 3 |
| 5.40 EQ | 38 | 15.0 | 81.3 | 22.7 | 7 |
| 6.72 EQ | 34 | 10.7 | 85.0 | 6.4 | 11 |
| Spray Date: D3 | | | | | |
| 1.68 EQ | 62 | 98.3 | 5.0 | 121.2 | 1 |
| 3.36 EQ | 55 | 98.3 | 43.3 | 84.2 | 3 |
| 5.40 EQ | 52 | 71.7 | 52.3 | 61.0 | 6 |
| 6.72 EQ | 50 | 45.0 | 58.7 | 35.0 | 6 |
| Spray Date: D4 | | | | | |
| 1.68 EQ | 60 | 100.0 | 2.7 | 102.8 | 2 |
| 3.36 EQ | 65 | 100.0 | 9.3 | 112.4 | 0 |
| 5.40 EQ | 62 | 100.0 | 32.2 | 97.3 | 5 |
| 6.72 EQ | 59 | 98.3 | 35.3 | 90.8 | 26 |
| Spray Date: D5 | | | | | |
| 1.68 EQ | 62 | 96.7 | 12.0 | 123.1 | |
| 3.36 EQ | 62 | 100.0 | 15.3 | 107.6 | |
| 5.40 EQ | 61 | 100.0 | 23.7 | 93.1 | |
| 6.72 EQ | 59 | 98.3 | 65.7 | 66.9 | |
| A McNair 1003 Control | 60 | 100.0 | 1.8 | 98.4 | — |
| Spray Date: D2 | | | | | |
| 1.68 EQ | 58 | 62.5 | 27.5 | 50.9 | — |
| 3.36 EQ | 42 | 35.0 | 93.0 | 16.0 | 13 |
| 5.40 EQ | 36 | 7.5 | 97.0 | 3.1 | 35 |
| 6.72 EQ | 27 | 5.0 | 100.0 | .9 | 14 |
| Spray Date: D3 | | | | | |
| 1.68 EQ | 63 | 75.0 | .0 | 70.6 | 1 |
| 3.36 EQ | 54 | 40.0 | 23.3 | 46.2 | 26 |
| 5.40 EQ | 46 | 23.3 | 66.7 | 18.3 | 30 |
| 6.72 EQ | 37 | 9.0 | 76.3 | 5.7 | 18 |
| Spray Date: D4 | | | | | |
| 1.68 EQ | 66 | 88.3 | .7 | 80.7 | 2 |
| 3.36 EQ | 66 | 88.3 | 16.7 | 64.4 | 14 |
| 5.40 EQ | 51 | 25.0 | 51.7 | 29.5 | 16 |
| 6.72 EQ | 51 | 31.7 | 52.3 | 30.2 | 31 |
| Spray Date: D5 | | | | | |
| 1.68 EQ | 63 | 100.0 | .0 | 102.5 | 0 |
| 3.36 EQ | 62 | 90.0 | 7.3 | 85.6 | 2 |
| 5.40 EQ | 61 | 78.3 | 16.3 | 67.8 | 13 |
| 6.72 EQ | 52 | 50.0 | 46.3 | 44.5 | 30 |
| C McNair 1003 Control | 66 | 100.0 | 1.8 | 98.4 | — |
| Spray Date: D2 | | | | | |
| 1.68 EQ | 58 | 65.0 | 56.0 | 51.3 | 16 |
| 3.36 EQ | 46 | 30.0 | 70.5 | 27.4 | 10 |
| 5.40 EQ | 45 | 25.0 | 96.0 | 21.5 | 10 |
| 6.72 EQ | 35 | 10.0 | 90.0 | 5.9 | 14 |
| Spray Date: D3 | | | | | |
| 1.68 EQ | 65 | 95.0 | .0 | 91.0 | 2 |
| 3.36 EQ | 60 | 53.3 | 10.0 | 65.6 | 7 |
| 5.40 EQ | 56 | 38.3 | 46.0 | 42.3 | 25 |
| 6.72 EQ | 52 | 33.3 | 74.3 | 24.6 | 32 |
| Spray Date: D4 | | | | | |
| 1.68 EQ | 66 | 96.7 | 1.7 | 83.3 | 3 |
| 3.36 EQ | 61 | 85.0 | 39.7 | 73.1 | 15 |
| 5.40 EQ | 55 | 68.3 | 61.7 | 41.6 | 45 |
| 6.72 EQ | 54 | 63.3 | 72.3 | 38.6 | 40 |
| Spray Date: D5 | | | | | |
| 1.68 EQ | 61 | 98.3 | 1.7 | 85.7 | 0 |
| 3.36 EQ | 61 | 91.7 | 9.7 | 77.9 | 5 |
| 5.40 EQ | 61 | 80.0 | 34.7 | 77.5 | 14 |
| 6.72 EQ | 57 | 66.7 | 41.7 | 62.5 | 22 |

EXAMPLE 6

The following Example summarizes the field and growth chamber results in the evaluation of several candidate gametocides applied to wheat. The evaluation procedures were essentially those described in Examples 1 and 2 above.

The compounds tested conformed to the following formula.

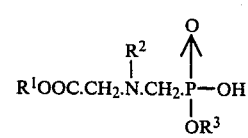

$$R^1OOC.CH_2.N.CH_2.P-OH$$

(with $R^2$ on N and $OR^3$ on P)

The compounds tested (A through E) had specific formulae as follows:

| Compound | $R^1$ | $R^2$ | $R^3$ |
|---|---|---|---|
| A[1] | H | H | OH<br>$-(CH_2)_4CH-CH_2OH$ |

-continued

| Compound | $R^1$ | $R^2$ | $R^3$ |
|---|---|---|---|
| B[(2)] | $\oplus[NH_3{-}CH(CH_3)_2]$ | H | $-CH_2\overset{\overset{\displaystyle OH}{\mid}}{CH}-CH_2OH$ |
| C | $-C_2H_5$ | $-COCF_3$ | $-CH_2.\overset{\overset{\displaystyle OH}{\mid}}{CH}-CH_2OH$ |
| D[(3)] | H | H | (a) $-CH_2.\overset{\overset{\displaystyle OH}{\mid}}{CH}.CH_2.OC(Ph)_3$ and (b) $-\overset{\overset{\displaystyle CH_2OH}{\mid}}{CH}.CH_2OC(Ph)_3$ |
| E[(3)] | H | H | (a) $-CH_2-\overset{\overset{\displaystyle OH}{\mid}}{CH}-CH_2OCH_2Ph$ and (b) $-\overset{\overset{\displaystyle CH_2OH}{\mid}}{CH}.CH_2OCH_2OCH_2Ph$ |

[(1)] with 0.4/mole NaCl and 0.4/mole H$_2$O
[(2)] with 0.75/mole of H$_2$O
[(3)] mixture of isomers with structures indicated The gametocidal activity and plant toxicity results are set forth in Table V.

TABLE V

| Compound | Field | | Growth Chamber |
|---|---|---|---|
| A | 2.24 Kg/H | moderate activity, slight toxicity | — |
|   | 8.96 Kg/H | very active, toxicity |   |
| B | 2.24 Kg/H | moderate activity, slight toxicity | 7.28 Kg/H Active |
|   | 4.48 Kg/H | very active, slight toxicity |   |
| C | — | — | 3.36 Kg/H Active |
| D | 5.6 Kg/H | slight activity, low toxicity | — |
| E | 2.24 Kg/H | moderate activity, slight toxicity | — |
|   | 4.48–6.72 Kg/H | active, toxic |   |

EXAMPLE 7

The following example was designed to evaluate the potential for retention of female fertility in wheat. Winter wheat cultivars were planted and evaluated as for Example 2. In this example, large plots, 1.5 × 1.5M were treated with the themical when the heads of the plants had reached 6 cm in length.

| CULTIVAR | VEG SCORE | PLANT HEIGHT | SEEDS PER HEAD | % MALE STERILITY | GRAIN YIELD | % FEMALE FERTILITY | % HYBRID SEED |
|---|---|---|---|---|---|---|---|
| B393 | | | | | | | |
| Control | 100 | 80 | 24.3 | 0 | 877 | 100 | 0 |
| Treated | 85 | 65 | 0.2 | 99 | 379 | 43 | 80 |
| Vona | | | | | | | |
| Control | 100 | 81 | 34 | 0 | 913 | 100 | 0 |
| Treated | 48 | 49 | 6.9 | 80 | 92 | 10 | 80 |
| Auburn | | | | | | | |
| Control | 100 | 87 | 34 | 0 | 1159 | 100 | NT |
| Treated | 70 | 67 | 6.1 | 82 | 470 | 40 | NT |
| McNair 1003 | | | | | | | |
| Control | 100 | 91 | 30 | 0 | 1019 | 100 | NT |
| Treated | 50 | 57 | 2.8 | 91 | 138 | 13 | NT |
| Titan | | | | | | | |
| Control | 100 | 94.5 | 33 | 0 | 990 | 100 | NT |
| Treated | 90 | 82.75 | 1.8 | 95 | 454 | 46 | NT |

EXAMPLE 8

This example demonstrates the relative field performance of 3 derivatives described in this invention. Winter wheat plants were cultivated and evaluated as described in Example 2. Compounds were sprayed when the heads of the plants had reached 4 cm in length at a rate equivalent to 4.5 lbs./A of compound A.

| Compound | R |
|---|---|
| A | $-CH_2.CH(OH).CH_2OH$ |
| B | $-CH_2-CH_2-OH$ |

| Compound | R |
|---|---|
| C | —CH$_2$—CH$_2$—CH$_2$—OH |

The compounds used conform to the formula:

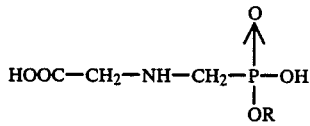

| COMPOUND | GENOTYPE | CULM HEIGHT | VEG SCORE | % MALE STERILITY | GRAIN YIELD (GMS) | % HYBRID SEED |
|---|---|---|---|---|---|---|
| Controls | B393 | 62 | 100 | 4 | 115 | 0 |
|  | McNair 1003 | 66 | 100 | 2 | 98 | 0 |
| A | B393 | 59 | 85 | 75 | 15 | 23 |
|  | McNair 1003 | 47 | 67 | 63 | 37 | 50 |
| B | B393 | 61 | 100 | 24 | 93 | 5 |
|  | McNair 1003 | 55 | 68 | 62 | 42 | 45 |
| C | B393 | 58 | 72 | 29 | 74 | 4 |
|  | McNair 1003 | 61 | 78 | 16 | 68 | 13 |

What is claimed is:

1. A process for the production of hybrid seed which comprises applying to a plant, at a time after initiation of sexual development, but before sexual maturity, a compound having the formula:

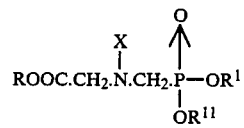

wherein R is hydrogen or a C$_1$-C$_4$ alkyl; R$^1$ is a hydroxyalkyl group having from 2 to 8 carbon atoms, 1 to 6 hydroxyl groups and 0 or 1 —O—CH$_n$[phenyl]$_{3-n}$ substituent wherein n is from 0 to 3; R$^{11}$ is hydrogen; and X is hydrogen or a —COCF$_3$ group; as well as agronomically acceptable salts of such compounds wherein said compound is applied in a quantity sufficient to render at least 95% of the plants' male gametes sterile while leaving at least 40% of the female gametes viable, causing the female gametes to be fertilized with pollen from a different cultivar of the same plant variety, and subsequently harvesting hybrid seed from said plant.

2. A process according to claim 1 in which the plant is a monocotylodon.

3. A process according to claim 2 in which the plant is wheat.

4. A process for hybridizing wheat which comprises applying an effective amount of a glyceryl monoester of glyphosate to a wheat plant, at a time from 2 to 20 days before flower opening, so as to kill at least 95% of the male gametes while leaving at least 40% of the female gametes viable, pollinating the wheat using pollen from a different cultivars and later harvesting the hybridized seed produced thereby.

* * * * *

UNITED STATES PATENT AND TRADEMARK OFFICE
CERTIFICATE OF CORRECTION

PATENT NO. :       4,735,649
DATED       :  4/5/88
INVENTOR(S) :  Om P. Dhingra, John E. Franz, Geoffrey Keyes,
           Dale F. Loussaert, and Cynthia S. Mamer It is certified that error appears in the above-identified patent and that said Letters Patent is hereby corrected as shown below:

Column 7, Table I under "Rate" "1.68 Kg/H" should be --16.8--.

Column 9, Table II, line 42, the numbers "62, 100.0, 4.1, 115.2 and 0" should be after the word "(Control)". In other words, they are on the wrong line.

Column 13, line 45, Table IV, the numbers "62, 100.0, 4.1, 115.2 and -" should be after the word "Control". In other words, they are on the wrong line.

In Column 14, line 25, Table IV, the numbers "66, 100.0, 1.8, 98.4 and -" should be after the word "Control". In other words, they are on the wrong line.

Signed and Sealed this

Sixth Day of June, 1989

Attest:

DONALD J. QUIGG

Attesting Officer

Commissioner of Patents and Trademarks